United States Patent [19]

Edwards et al.

[11] Patent Number: 5,294,636

[45] Date of Patent: Mar. 15, 1994

[54] CRYSTALLINE FORM OF INDOLE DERIVATIVE AND PHARMACEUTICAL METHOD THEREOF

[75] Inventors: Martin P. Edwards, Bollington; John D. Sherwood, Congleton, both of England

[73] Assignee: Imperial Chemical Industries plc, London, England

[21] Appl. No.: 805,426

[22] Filed: Dec. 11, 1991

[30] Foreign Application Priority Data

Dec. 12, 1990 [GB] United Kingdom ............... 9027018

[51] Int. Cl.$^5$ ..................... A61K 31/40; C07D 209/14
[52] U.S. Cl. ..................................... 514/415; 548/507
[58] Field of Search ........................ 514/415; 548/507

[56] References Cited

U.S. PATENT DOCUMENTS 4,161,516 7/1979 Bell ........................ 424/14

FOREIGN PATENT DOCUMENTS 199543 10/1986 European Pat. Off. .

*Primary Examiner*—Mary C. Lee
*Assistant Examiner*—Jacqueline Haley
*Attorney, Agent, or Firm*—Thomas E. Jackson

[57] ABSTRACT

A physical form of N-[4-[5-(cyclopentyloxycarbonyl)amino-1-methyl-indol-3-ylmethyl]-3-methoxybenzoyl]-2-methylbenzenesulphonamide substantially free of other physical forms, which form is crystalline, has an X-ray powder diffraction pattern with specific peaks occuring at $2\theta = 8.1$, 13.7, 16.4, 20.5 and 23.7° and an infra-red spectrum (0.5% in KBr) having sharp peaks at 3370, 1670, 1525, 1490, 1280, 890, 870 and 550 cm$^{-1}$, a process for its preparation and pharmaceutical compositions containing it. Also disclosed is a flowable preparation of the physical form which is in the form of soft pellets, and a process for obtaining this preparation.

6 Claims, 5 Drawing Sheets

CRYSTALLINE FORM OF INDOLE DERIVATIVE AND PHARMACEUTICAL METHOD THEREOF

The present invention relates to heterocyclic compounds. More particularly, it relates to a new physical form of a heterocyclic amide derivative, to a process for the preparation of this physical form, and to a pharmaceutical composition containing it.

Before a compound in the solid state can be formulated in a pharmaceutical composition, a physical form of the compound is sought which is physically stable and can be prepared substantially free of other physical forms. This latter requirement is important because different physical forms can have markedly different bioavailabilities.

European patent application publication number EP-A2-0199543 discloses certain heterocyclic amide derivatives which antagonise the pharmacological actions of one or more of the arachidonic acid metabolites known as leukotrienes. One of these heterocyclic amide derivatives is N-[4-[5-(cyclopentyloxycarbonyl)amino-1-methylindol-3-ylmethyl]-3-methoxybenzoyl]-2-methylbenzenesulphonamide, hereinafter referred to as compound 1. Example 105 in EP-A2-0199543 discloses the preparation of compound 1 and its isolation in the solid state. The material obtained had a melting point of 138°–140° C.

It has been found that compound 1 can be isolated in the solid state as a material having a range of different physical properties, depending upon the method of isolation. This ability is due to the fact that compound 1 can exist in more than one physical form, and mixtures of these forms can be isolated.

A method of preparing a physical form of compound 1 substantially free of other physical forms has now been found, and this form substantially free of other physical forms is provided as the present invention.

Accordingly, the present invention provides a new physical form of N-[4-[5-(cyclopentyloxycarbonyl)amino-1-methylindol-3-ylmethyl]-3-methoxybenzoyl]-2-methylbenzenesulphonamide substantially free of other physical forms, which form is crystalline, has an X-ray powder diffraction pattern with specific peaks occuring at $2\theta = 8.1°$, 13.7°, 16.4°, 20.5° and 23.7° and an infra-red spectrum (0.5% in KBr) having sharp peaks at 3370, 1670, 1525, 1490, 1280, 890, 870 and 550 $cm^{-1}$.

The new physical form of compound 1, which is referred to hereinafter as form X, is physically stable and can be prepared substantially free of other physical forms.

Where reference is made in this specification to form X substantially free of other physical forms, it preferably means that at least 90% by weight of the compound 1 present is in that physical form.

The advantageous nature of form X may be demonstrated by comparing its properties with those of other physical forms of compound 1.

One other physical form of compound 1 is a monohydrate of compound 1 which is crystalline, has an infra-red spectrum (0.5% in KBr) having sharp peaks at 3560, 1690, 1660, 1540, 1440, 1165, 880 and 858 $cm^{-1}$, and an X-ray powder diffraction pattern having peaks at $2\theta = 10.0°$, 11.2°, 14.6°, 19.8° and 23.0°. It is referred to hereinafter as form B.

Form B may be prepared substantially free of other physical forms by crystallisation from hot aqueous acetone. In particular, it may be prepared by dissolving a source of compound 1 in aqueous acetone at an elevated temperature, adding more water, and allowing the resultant mixture to cool. The crystalline product may be dried at an elevated temperature, for example at about 60° C. or below. If it is desired to start from an impure source of compound 1, it has been found advantageous to triturate this impure source with hot toluene/ethyl acetate prior to the crystallisation.

Form B has been found to be more difficult to prepare substantially free of other physical forms than form X. In particular, it has been found that after form B has been crystallised and filtered off, it is difficult to remove the residual organic solvent without losing some of the water of crystallisation.

Another physical form of compound 1 is amorphous, has an infra-red spectrum (0.5% in KBr) having sharp peaks at 1690, 1530, 1490, 1420, 1155, 1060, 862 and 550 $cm^{-1}$. This amorphous form of compound 1 is referred to hereinafter as form A. Because form A is amorphous, it is also characterised by an X-ray powder diffraction pattern having no discernable peaks.

Form A may be prepared substantially free of other physical forms by dehydrating form B, prepared as described above, at a temperature of about 120° C. under vacuum.

Form A has been found to be physically unstable in the presence of chlorofluorocarbon aerosol propellants, and is therefore unsuitable for use in an aerosol formulation. In particular, when suspended in a chlorofluorocarbon aerosol propellant, it has been found to change to a new, crystalline form, the crystals of which have been found to grow beyond a size suitable for use in a metered dose inhaler.

Form X has been found to be stable in the presence of chlorofluorocarbon aerosol propellants.

Each of the forms X, A, and B may conveniently be characterised for example by their X-ray powder diffraction pattern alone, or their infra-red pattern alone.

BRIEF DESCRIPTION OF THE DRAWINGS

In this specification, infra-red spectra were determined using a 0.5% dispersion of sample material in a potassium bromide disc over the wave number range 4000 to 400 $cm^{-1}$. Examples of infra-red spectra for each of forms X, A and B are given in FIGS. 1, 2 and 3 hereinafter.

X-ray powder diffraction spectra were determined using 2 g of sample material mounted in a Philips standard deep pack holder over the scanning range of 4°–40° 2Θ counting for 4 seconds per point at 0.02° intervals to produce a trace of spacings against intensity for this range. Examples of X-ray powder diffraction spectra for each of forms X, A and B are given in FIGS. 4, 5 and 6 hereinafter.

Figure 1:
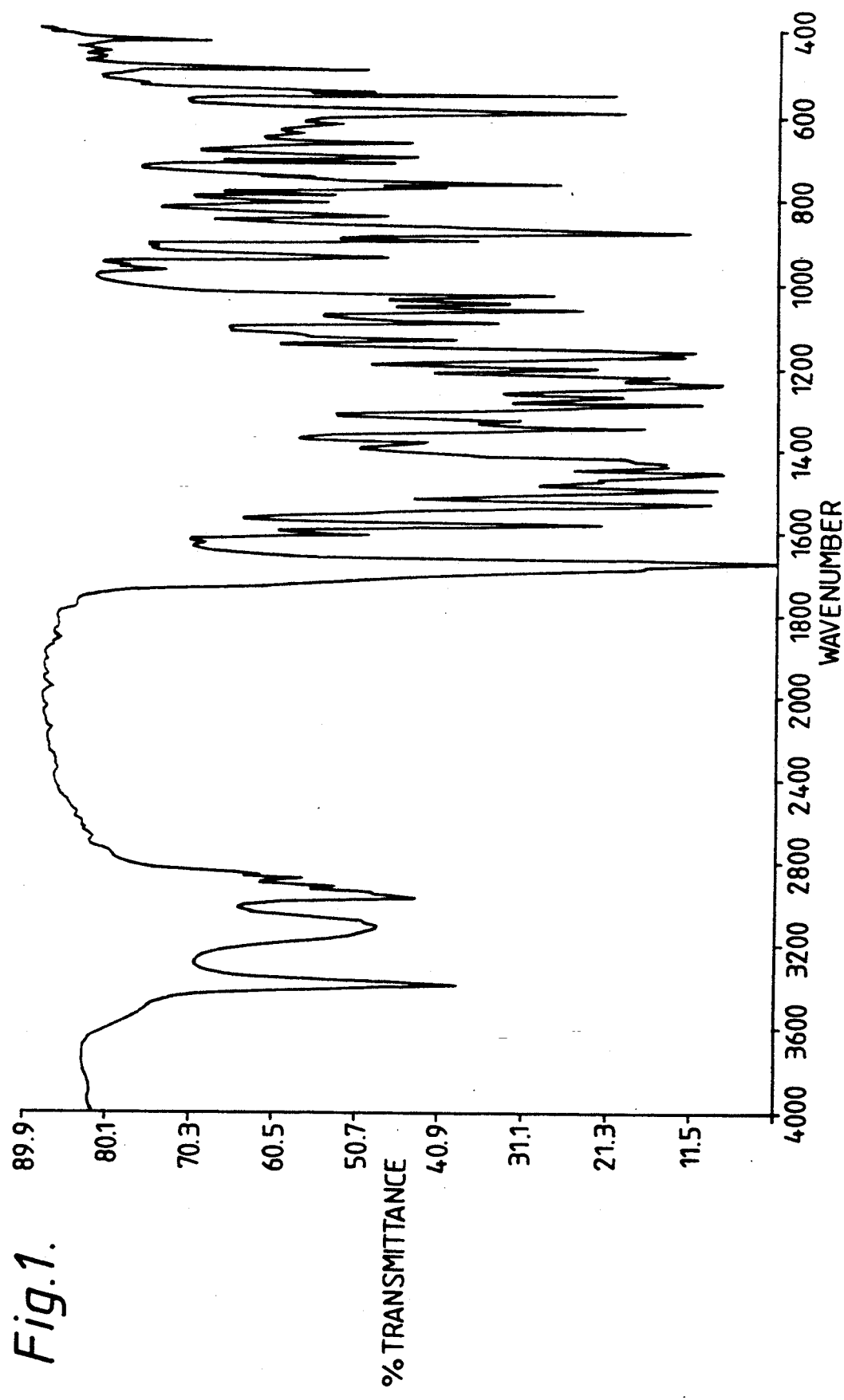
Figure 2:
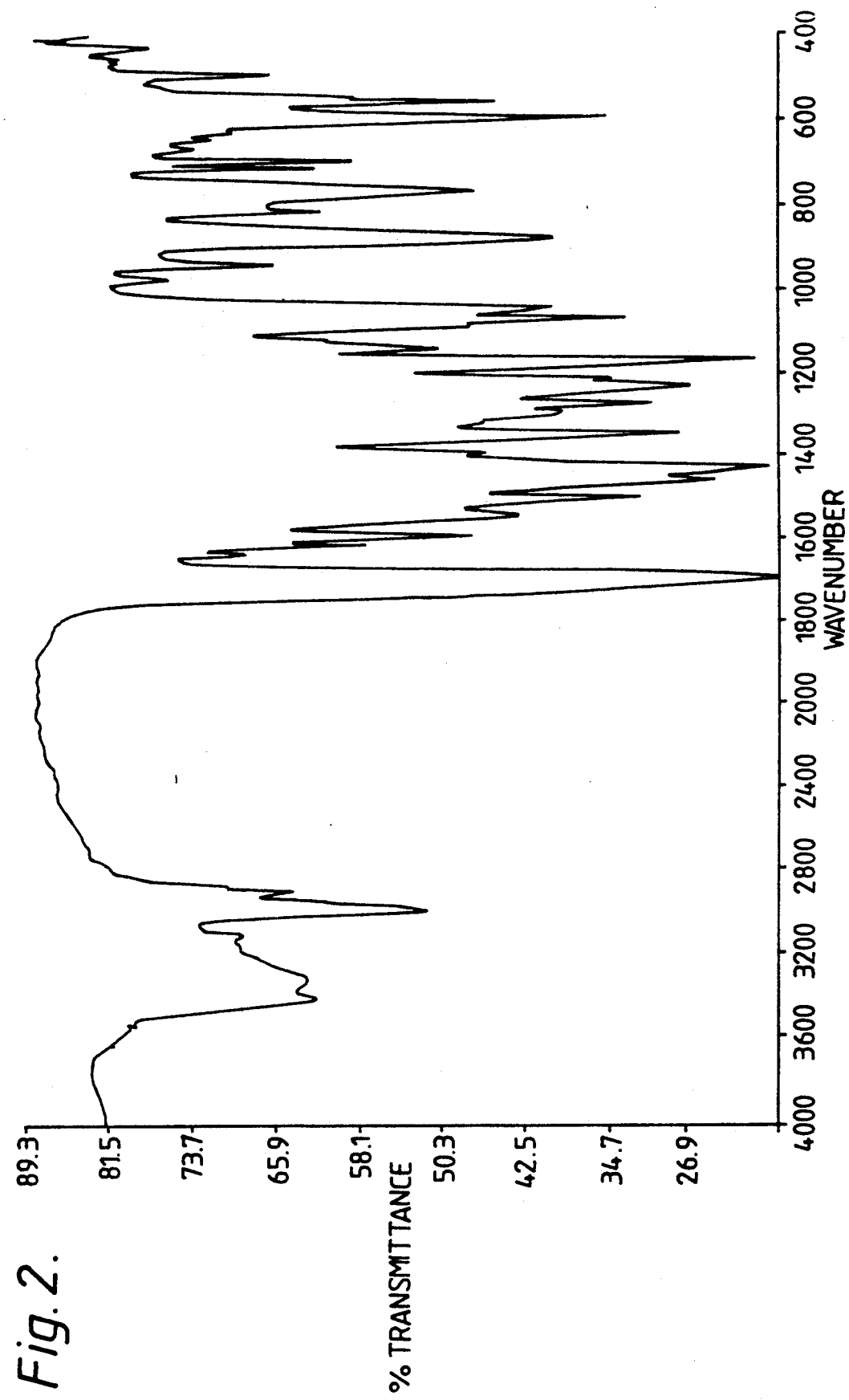
Figure 3:
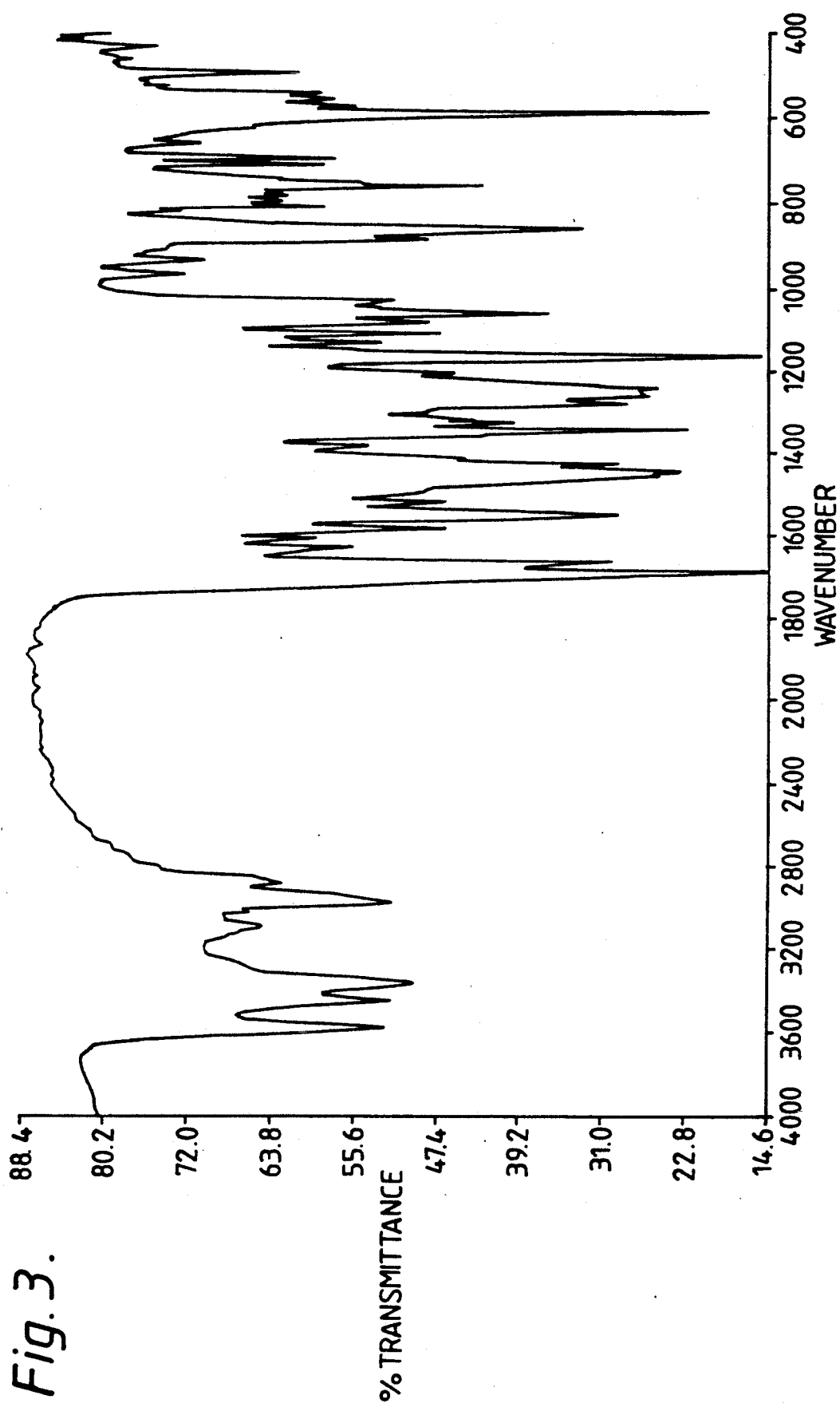
Figure 4:
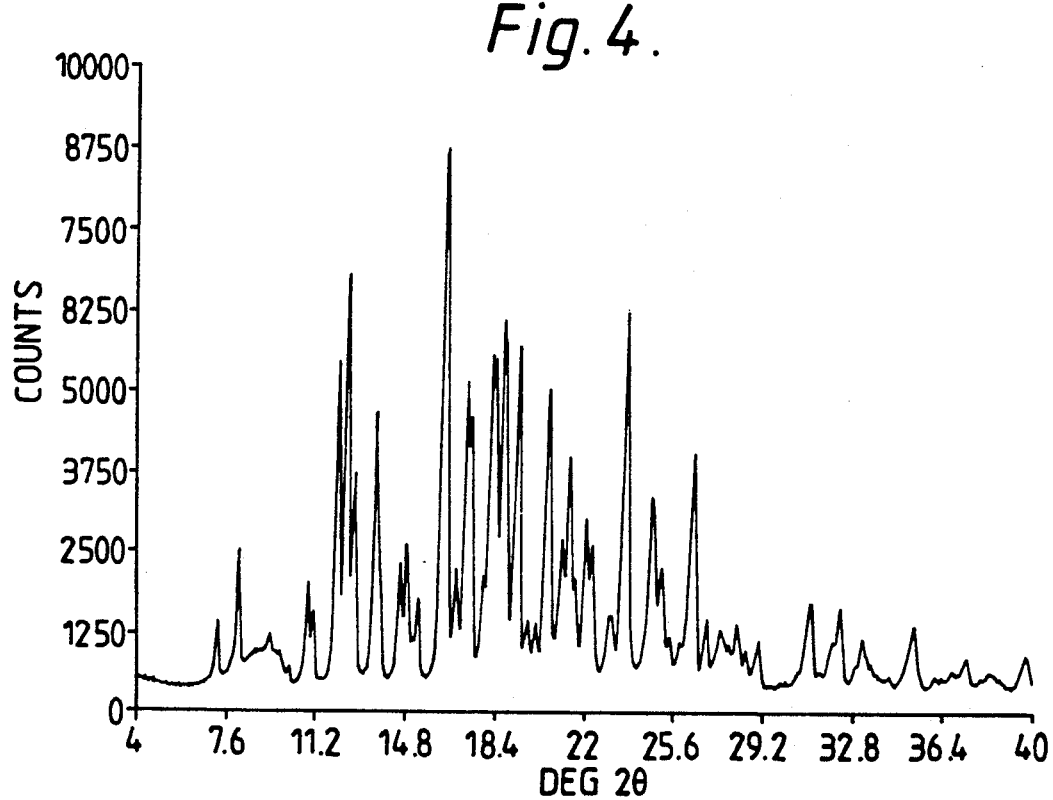
Figure 5:
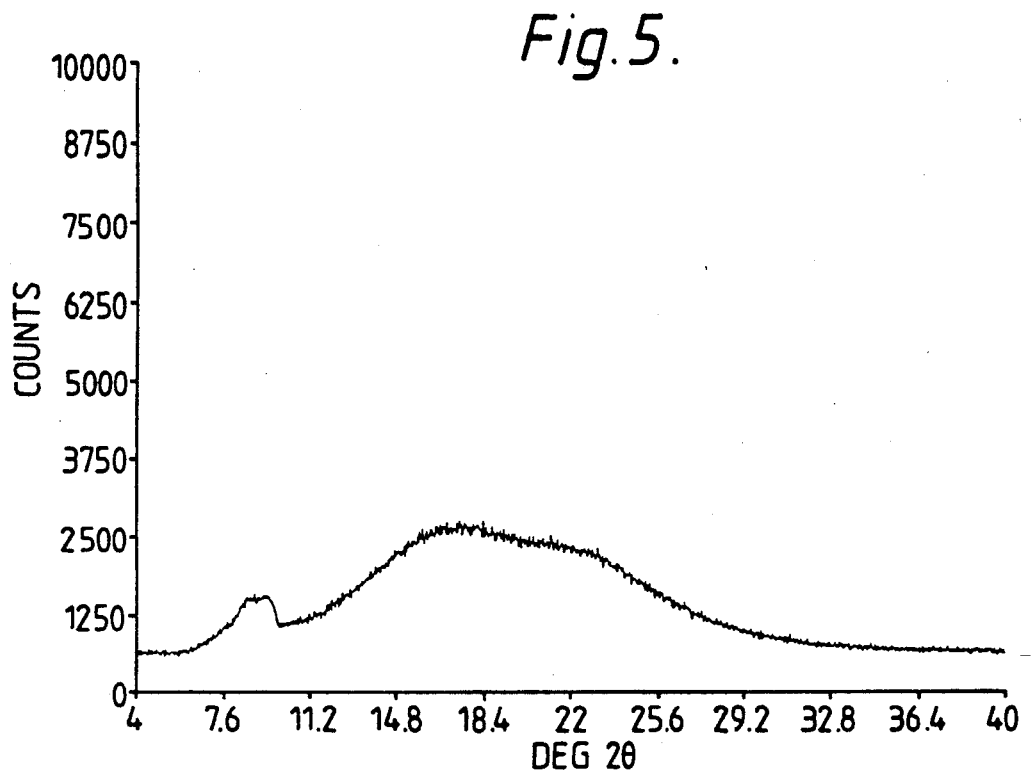
Figure 6:
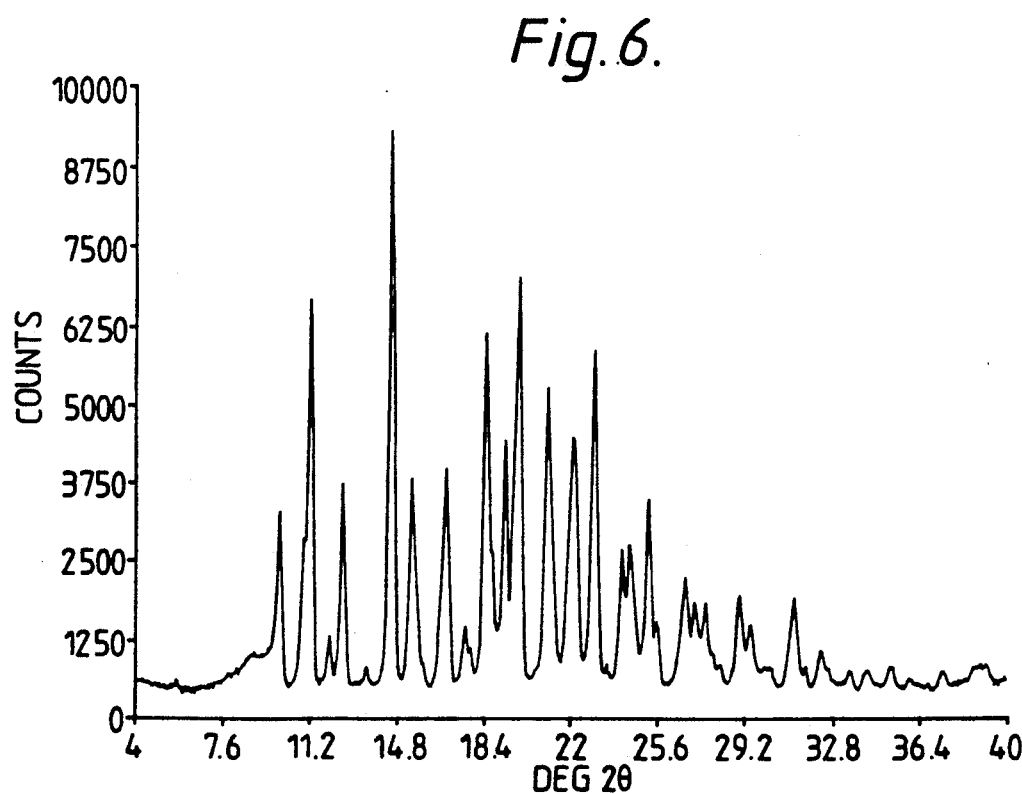

The melting points of each of the forms X, A and B generally depend upon their level of purity. Typically, form X has been found to have a melting point of about 190° C., for example about 200° C.; form A between 115° C. and 140° C., for example about 124° to 132° C.; and form B about 140° to 160° C., for example from 145° to 155° C. Form B has been observed to lose water at a temperature of from about 60° C., and may not show a sharp melting point.

According to another aspect, the invention provides a process for the preparation of form X substantially free of other physical forms, which comprises dissolving a source of compound 1 in hot aqueous acetone, reducing the volume of the resultant solution by evaporation, adding toluene and further reducing the volume by evaporation.

If it is desired to employ material which is a relatively impure source of compound 1, such material may advantageously be triturated with hot toluene/ethyl acetate prior to the crystallisation step.

As stated previously, compound 1 possesses leukotriene antagonist properties. Thus, it antagonises the actions of one or more of the arachidonic acid metabolites known as leukotrienes, for example, $C_4$, $D_4$ and/or $E_4$, which are known to be powerful spasmogens (particularly in the lung), to increase vascular permeability and have been implicated in the pathogenesis of asthma and inflammation (see J. L. Marx, Science, 1982, 215, 1380-1383) as well as of endotoxic shock (see J. A. Cook, et al., J. Pharmacol. Exp. Ther., 1985, 235, 470) and traumatic shock (see C. Denzlinger, et al., Science, 1985, 230, 330). Compound 1 is thus useful in the treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, psoriasis, as well as vasospastic cardiovascular disease, and endotoxic and traumatic shock conditions.

Form X may be administered by itself, for example by inhalation as a micronised powder, or in a pharmaceutical composition.

According to another aspect, the invention provides a pharmaceutical composition, which comprises form X substantially free of other physical forms and a pharmaceutically acceptable carrier.

The pharmaceutical composition may be formulated in a conventional manner, and may typically be in the form of tablets, capsules or suspensions for oral administration; in the form of suppositories for rectal administration; in the form of suspensions for parenteral administration; in the form of suspensions for inhalation administration by metered dose inhaler or nebuliser; and in the form of powders together with pharmaceutically acceptable inert solid diluents such as lactose for administration by inhalation.

As stated hereinbefore, form X is especially suitable for use in a metered dose inhaler. According to a preferred aspect, therefore, the invention provides a pharmaceutical composition suitable for administration by a metered dose inhaler, which comprises form X substantially free of other physical forms and a pharmaceutically acceptable propellant.

The non toxic pharmaceutically acceptable propellant may be any of those conventionally used in metered dose inhalers. Examples of propellants include chlorofluorocarbons, for example trichlorofluoromethane, dichlorodifluoromethane and dichlorotetrafluoroethane; and 1,1,1,2-tetrafluoroethane.

The pharmaceutical composition suitable for administration by a metered dose inhaler may further comprise one or more other ingredients conventionally used in metered dose inhalers, for example oleic acid, sorbitan trioleate or lecithin.

The mean mass aerodynamic diameter of form X used in the aerosol composition is conveniently less than 50 microns, preferably in the range of from 1 to 50 microns, more preferably 1 to 10 microns, especially 1 to 5 microns.

The amount of form X present in the aerosol composition is conveniently from 0.01 to 10% by weight, preferably from 0.03 to 2%, more preferably from 0.05 to 1%.

The amount of form X administered to a patient will depend upon the weight of the patient and the severity of the disorder being treated, and the route of administration. Conveniently, a unit aerosol dose will comprise from 0.01 to 2.0 mg of form X, preferably from 0.02 to 1.0 mg, more preferably from 0.05 to 0.6 mg. Administration may take place from 1 to 8 times per day, preferably from 1 to 4 times per day. A typical daily dose for a 70 kg patient will be from 0.01 to 16 mg, preferably 0.02 to 4 mg.

It has been found that micronised form X has very poor flow characteristics, and tends to adhere to many different types of surface. These properties are disadvantageous, because a powder with poor flow characteristics is difficult to handle on a manufacturing scale. Furthermore, such a powder is unsuitable for use in a dry powder inhaler, especially one that utilises volumetric metering.

A flowable state of form X has now been found, and is provided as a further feature of the invention.

Accordingly, the invention provides form X in the form of soft pellets consisting of an agglomeration of particles, at least 90% of which have a diameter of less than 10 microns, which pellets have a diameter in the range of from 50 to 900 microns.

The diameter of the pellets may be, for example in the range of from 75 to 250 microns, such as from 100 to 200 microns, or from 200 to 500 microns, such as from 250 to 400 microns, depending upon their intended use.

It has been found that form X in the form of soft pellets as defined above has good flow characteristics. Furthermore, it has been found that the pellets readily break down to the original particles when exposed to shear forces. These properties are particularily desirable in a powder intended for use in a dry powder inhaler, especially one that utilises volumetric metering. Thus, in a dry powder inhaler which utilises volumetric metering, it is important for powder to be able to flow freely from a powder reservoir into a dosing hole. It is also important, in any dry powder inhaler, that any agglomerates of particles are broken up before leaving the device, otherwise they will be too large to be able to penetrate into the lungs.

According to another aspect, the invention provides a process for obtaining form X in the form of soft pellets, which comprises extruding micronised form X through a sieve having apertures with a diameter in the range of from 150 to 700 microns, rolling the extruded material, and then screening the rolled material.

The micronised form X is preferably extruded through a sieve having apertures with a diameter in the range of from 175 to 600 microns. The extrusion may conveniently be performed by passing the surface of a blade across powder on the surface of the sieve.

The function of the rolling step in the process is to strengthen the agglomerates of particles formed in the extrusion step, and to mould them into a spherical shape. The rolling may conveniently be effected by allowing the agglomerates to tumble in a rotating vessel, preferably a cylindrical vessel.

The screening step removes over and undersized pellets. It is conveniently performed using two sieves with apertures defining the upper and lower desired pellet diameters.

The following Examples illustrate the invention.

EXAMPLE 1

Preparation of Form X a) Preparation of an Impure Source of Compound 1

Methyl 3-methoxy-4-(1-methyl-5-nitroindol-3-ylmethyl)benzoate (prepared as described in Example 4 of EP-A2-0199543) was converted into the free acid by treatment with aqueous sodium hydroxide. The free acid was then converted into the acid chloride by treatment with thionyl chloride in dichloromethane. The acid chloride was then reacted o-toluenesulphonamide in dichloromethane in the presence of 2.2 equivalents of 4-dimethylaminopyridine to afford the dimethylaminopyridine salt of 4-(1-methyl-5-nitroindol-3-ylmethyl)-3-methoxybenzoyl-2-methylbenzenesulphonamide.

A solution of the dimethylaminopyridine salt of 4-(1-methyl-5-nitroindol-3-ylmethyl)-3-methoxybenzoyl-2-methylbenzenesulphonamide (30 g) in 2-methoxyethanol (130 ml) and concentrated sodium hydroxide liquor (3.2 ml) was charged to a nitrogen-purged flask containing 10% palladium on charcoal (3.3 g of a 60.9% water-wet paste). The mixture was then stirred under a hydrogen atmosphere at a pressure of 3 bar for 2.5 hours. The mixture was then filtered through diatomaceous earth, and washed through with 2-methoxyethanol (37.5 ml). To the combined liquors was added cyclopentyl chloroformate (9.2 ml), and the mixture allowed to stir under an atmosphere of nitrogen overnight. The temperature was then adjusted to 30°-33° C., and 0.8M hydrochloric acid (68 ml) was added over 20 minutes with vigorous agitation. The mixture was then cooled to 15°-20° C. and stirred for one hour. The crystalline product was then filtered off, washed with water and dried at 50° C. It was then used in the next step.

b) Trituration of Impure Compound 1

60 g (0.101 gmol) of the product of step a), toluene 240 ml (4 volumes) and ethyl acetate 150 ml (2.5 voluumes) were slowly heated to reflux and 30 ml (0.5 volumes) of distillate were collected to remove most of the released water. The mixture was heated under reflux for one hour (88°-90° C.) and was then cooled to 10°-15° C. After stirring for three hours at 10°-15° C., the solid was filtered through a glass sinter and washed with a 2:1 mixture of toluene (80 ml) and ethyl acetate (40 ml). The product was then dried to constant weight on the sinter to afford 53.2 g of dry compound 1 (yield 91.5%).

c) Preparation of Form X

The product of step b) (30.0 g, 0.0521 g mol) was dissolved in acetone (150 ml) and water (4.7 ml) by gentle heating to reflux, and the solution screened through a sintered glass funnel. The filtrate was heated to boiling and 90 ml distillate collected. Toluene (120 ml) was added and a further 75 ml distillate collected. More toluene (120 ml) was added and an additional 75 ml distillate collected. After heating for a further hour at reflux, the mixture was cooled to 15°-20° C., and the product collected and washed with toluene (2×30 ml). The yield after drying on the sinter funnel was 29.5 g (98.3%).

Preparation of Form B 30.0 g of the product of step b), 210 ml acetone and 12 ml water were charged to a 500 ml reaction flask. The mixture was then heated under reflux for 15 minutes, and was then screened at 45°-50° C. through a diatomaceous earth pad on a glass sinter directly into a 500 ml reaction flask. The flask and sinter were washed with a mixture of acetone (60 ml) and water (3 ml). The combined liquids were then stirred in a water bath at approximately 40° C. and water (120 ml) was added over five minutes. The mixture oiled out at first, but then rapidly crystallised. The mixture was then cooled to 20° C. over one hour, stirred for two hours at 15°-20° C. and then filtered. The product was washed with water (60 ml), dried as far as possible on the sinter and then dried in an air oven at 60° C. (max.). The yield of form B was 30.0 g (97%).

It has been found that the drying conditions for form B must be strictly controlled in order to prevent loss of water.

Preparation of Form A

Form B prepared as described above (15.0 g) was placed in a 500 ml round bottomed flask which was then evacuated on a rotary evaporator at 20 mbara. The flask and contents were then immersed in an oil bath preheated to 118° C., and slowly rotated at this temperature for 6 hours. The mass was broken up on cooling to afford form A as a white powder.

EXAMPLE 2

Pharmaceutical Composition of Form X Suitable for Administration by a Metered Dose Inhaler

| Active ingredient | 0.02 g |
|---|---|
| Oleic acid | 0.01 g |
| (chlorofluorocarbon 11) | |
| Dichlorodifluoromethane | 10.5 g |
| (chlorofluorocarbon 12) | |
| Dichlorotetrafluoroethane | 4.5 g |
| (chlorofluorocarbon 114) | |

Oleic acid, and then micronised active ingredient were added to a tank containing the trichloromonofluoromethane. The mixture was then homogenised and transferred into an aerosol canister. A valve was then crimped onto the aerosol canister, and then the remaining chlorofluorocarbons were introduced into the canister through the valve.

Comparison of the Stability of Form X in an Aerosol Formulation with that of Form A Compositions comprising form X or form A were prepared as described in Example 2 and stored at various temperatures and humidity levels for 1, 3 and 6 months. Samples of the materials were then sprayed onto a microscope slide and examined under a microscope. The results are summarised in Tables 1 and 2.

Samples from each stability test were also studied by cascade impaction. The results are summarised in Tables 3 and 4.

The results of these comparative tests demonstrate the superiority of form X over form A in an aerosol formulation.

EXAMPLE 3

Pharmaceutical Composition of Form X Suitable for Administration by a Metered Dose Inhaler.

| Active ingredient | 0.02 g |
|---|---|
| Sorbitan trioleate | 0.04 g |
| Trichloromonofluoromethane | 7.0 g |

-continued

| | |
|---|---|
| (chlorofluorocarbon 11) | |
| Dichlorodifluoromethane | 13.0 g |
| (chlorofluorocarbon 12) | |

The composition was prepared by a method analogous to that described in Example 2.

TABLE 1

Microscopic Observations of Metered Dose Inhaler Formulation of Form X

| Storage conditions | Particle Characteristics |
|---|---|
| Initial | Highly crystalline irregularly shaped particles which are <5 μm some agglomerates (up to 12.5 μm) of these particles |
| 5° C. | |
| 1 month | NC |
| 3 months | NC |
| 6 months | NC |
| RT | |
| 1 month | NC |
| 3 months | NC |
| 6 months | NC |
| 30° C./80% RH | |
| 1 month | NC |
| 3 months | NC |
| 6 months | NC |
| 40° C. | |
| 1 month | NC |
| 3 months | NC |
| 6 months | NC |

NC = no change
RH = relative humidity
RT = room temperature

TABLE 2

Hieroscopic Observations of Metered Dose Inhaler Formulation of Form A

| Storage conditions | Particle Characteristics |
|---|---|
| Initial | needles |
| 4° C. | |
| 1 month | needles |
| 3 months | needles |
| 6 months | needles |
| RT | |
| 1 month | needles |
| 3 months | needles |
| 6 months | needles |
| 30° C./80% RH | |
| 1 month | needles |
| 3 months | needles |
| 6 months | needles, rods (many; up to 20 × 600 μm) |
| 40° C. | |
| 1 month | needles, rods (only a few; up to 6 × 173 μm) |
| 3 months | needles, rods (more; up to 15 × 289 μm) |
| 6 months | needles, rods (many; up to 20 × 150 μm) |

RH = relative humidity
RT = room temperature

TABLE 3

Summary of Cascade Impaction Results for Metered Dose Inhaler Product Containing Form X

| Storage Condition | MMAD (μm) | GSD |
|---|---|---|
| Initial | 3.94 | 1.67 |
| 5° C. | | |
| 1 month | 3.60 | 1.95 |
| 3 months | 3.60 | 1.64 |
| 6 months | 3.16 | 1.53 |
| RT | | |
| 1 month | 3.64 | 1.78 |
| 3 months | 3.53 | 1.66 |
| 6 months | 3.67 | 1.62 |
| 30° C./80% RH | | |
| 1 month | 3.74 | 1.89 |
| 3 months | 4.25 | 1.75 |
| 6 months | 3.98 | 1.66 |
| 40° C. | | |
| 1 month | 3.73 | 1.89 |
| 3 months | 3.76 | 1.64 |
| 6 months | 3.67 | 1.62 |

MMAD = mass median aerodynamic diaheter
GSD = geometric standard deviation
RT = room temperature
RH = relative humidity

TABLE 4

Summary of Cascade Impaction Results for Metered Dose Inhaler Product Containing Form A

| Storage Condition | MMAD (μm) | GSD |
|---|---|---|
| Initial | 2.00 | 1.82 |
| 4° C. | | |
| 1 month | 1.45 | 1.95 |
| 3 months | 1.32 | 1.74 |
| 6 months | 1.70 | 1.81 |
| RT | | |
| 1 month | 1.70 | 1.87 |
| 3 months | 1.53 | 1.77 |
| 6 months | 1.80 | 1.85 |
| 30° C./80% RH | | |
| 1 month | 1.76 | 1.77 |
| 3 months | 1.57 | 1.80 |
| 6 months | >>9.0 | — |
| 40° C. | | |
| 1 month | 1.41 | 1.76 |
| 3 months | 1.70 | 1.84 |
| 6 months | >>9.0 | — |

MMAD = mass median aerodynamic diameter
GSD = geometric standard deviation
RT = room temperature
RH = relative humidity

EXAMPLE 4

Tablet Formulation of Form X

| Granulating Material | mg/tablet |
|---|---|
| Active ingredient | 20 |
| Croscarmellose sodium | 5 |
| Polyvinylpyrrolidone | 4 |
| Microcrystalline cellulose | 74 |
| Lactose | 50 |
| Purified water for injection | 98 |
| Final Blend Material | |
| Dried milled granulation | 153 |
| Lactose | 20 |
| Croscarmellose sodium | 5 |
| Microcrystalline cellulose | 20 |
| Magnesium stearate | 2 |

The ingredients of the granulating material are wet granulated. The granules are then dried and milled. The dried milled granulation is then blended with the other ingredients of the final blend mixture and compressed into tablets.

EXAMPLE 5

Treatment of Micronised Form X to Improve its Flow Characteristics

Form X was micronised to produce a powder consisting of at least 98% by weight of particles having a diameter of less than 10 microns.

30 g of the powder was then placed in one heap on a brass sieve having an aperture size between 210 and 500 microns. The powder was then extruded through the apertures of the sieve using a stainless steel palette knife. The extrudate thus formed was then placed into a screw topped glass jar.

The glass jar was then placed on to a set of rollers, which were rotated at 100 rpm for between 8 and 20 minutes. The soft pellets thus formed were then sieved through an 850 micron sieve and then a 150 micron sieve, the fraction retained on the 150 micron sieve being the required product.

The soft pellets thus produced were free flowing and relatively dust free. However the pellets when sheared, for example in a twin impinger, broke back down to the powder's original particle size distribution. This indicates that the pellets are suitable for use in a multidose dry powder inhaler that utilises volumetric metering to measure out the doses.

What we claim is:

1. A physical form of N-[4-[5-(cyclopentyloxycarbonyl)amino-1-methyl-indol-3-ylmethyl]-3-methoxybenzoyl]-2-methylbenzenesulphonamide, which form is crystalline, has an X-ray powder diffraction pattern with specific peaks occuring at $2\theta=8.1°$, 13.7°, 16.4°, 20.5° and 23.7°; an infra-red spectrum (0.5% in KBr) having sharp peaks at 3370, 1670, 1525, 1490, 1280, 890, 870 and 550 $cm^{-}$; and a melting point in the range of 190° to 200° C.

2. A pharmaceutical composition, which comprises an effective amount of a physical form of N-[4-[5-(cyclopentyloxycarbonyl)amino-1-methyl-indol-3-ylmethyl]-3-methoxybenzoyl]-2-methylbenzenesulphonamide as claimed in claim 1 and a pharmaceutically acceptable carrier.

3. A pharmaceutical composition as claimed in claim 2, which composition is suitable for administration by a metered dose inhaler, and comprises a pharmaceutically acceptable propellant.

4. A composition as claimed in claim 3, in which the propellant comprises trichlorofluoromethane, dichlorodifluoromethane, dichlorotetrafluoroethane or 1,1,1,2-tetrafluoroethane.

5. A physical form of N-[4-[5-(cyclopentyloxycarbonyl)amino-1-methylindol-3-ylmethyl]-3-methoxybenzoyl]-2-methylbenzenesulphonamide substantially free of other physical forms, which form is crystalline, has an X-ray powder diffraction pattern with specific peaks occuring at $2\theta=8.1°$, 13.7°, 16.4°, 20.5 ° and 23.7°; an infra-red spectrum (0.5% in KBr) having sharp peaks at 3370, 1670, 1525, 1490, 1280, 890, 870 and 550 $cm^{-1}$; and a melting point in the range of 190° to 200° C. and which is in the form of soft pellets consisting of an agglomeration of particles, at least 90% of which have a diameter of less than 10 microns, which pellets have a diameter in the range of from 50 to 900 microns.

6. A method for antagonising one or more of the actions of leukotrienes in a living mammal, which comprises administering to said mammal an effective amount of a physical form of N-[4-[5-cyclopentyloxycarbonyl)amino-1-methylindol-3-ylmethyl]-3-methoxybenzoyl]-2-methylbenzene sulphonamide as claimed in claim 1.

* * * * *